United States Patent
Lee et al.

(10) Patent No.: US 9,738,574 B2
(45) Date of Patent: Aug. 22, 2017

(54) METHOD FOR PRODUCING BUTADIENE THROUGH OXIDATIVE DEHYDROGENATION REACTION

(71) Applicant: LG CHEM, LTD., Seoul (KR)

(72) Inventors: Jae Ik Lee, Daejeon (KR); Jeong Seok Lee, Daejeon (KR); Mi Kyung Kim, Daejeon (KR); Dae Hyeon Kim, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/034,815

(22) PCT Filed: May 15, 2015

(86) PCT No.: PCT/KR2015/004928
§ 371 (c)(1),
(2) Date: May 5, 2016

(87) PCT Pub. No.: WO2015/186915
PCT Pub. Date: Dec. 10, 2015

(65) Prior Publication Data
US 2016/0289145 A1    Oct. 6, 2016

(30) Foreign Application Priority Data

Jun. 3, 2014  (KR) .................. 10-2014-0067685
May 12, 2015  (KR) .................. 10-2015-0066060

(51) Int. Cl.
*C07C 5/48* (2006.01)
*C07C 7/00* (2006.01)
*C07C 7/04* (2006.01)

(52) U.S. Cl.
CPC ................ *C07C 5/48* (2013.01); *C07C 7/005* (2013.01); *C07C 7/04* (2013.01); *C07C 2523/18* (2013.01);
(Continued)

(58) Field of Classification Search
CPC ..... C07C 5/48; C07C 11/167; C07C 2523/18; C07C 2523/28; C07C 2523/31; C07C 7/005; C07C 7/04
See application file for complete search history.

(56) References Cited

U.S. PATENT DOCUMENTS

| | | |
|---|---|---|
| 2005/0171311 A1 | 8/2005 | Schindler et al. |
| 2008/0183024 A1 | 7/2008 | Klanner et al. |

(Continued)

FOREIGN PATENT DOCUMENTS

| | | |
|---|---|---|
| JP | S6092224 | 5/1985 |
| JP | S60126235 | 7/1985 |

(Continued)

*Primary Examiner* — Sharon Pregler
(74) *Attorney, Agent, or Firm* — Dentons US LLP

(57) ABSTRACT

The present invention relates to a method for producing butadiene through an oxidative dehydrogenation reaction. The production method according to the present invention may easily regulate an input ratio between oxygen and nitrogen that are used as raw material, such that a loss may be minimized of butadiene that is included in a second fraction stream (purge stream) and discharged to outside of the system. Consequently, an economic competitiveness of the process, such as a reduced raw material cost and an improved productivity may be realized.

7 Claims, 1 Drawing Sheet

(52) U.S. Cl.
CPC ...... *C07C 2523/28* (2013.01); *C07C 2523/31* (2013.01)

(56) References Cited

U.S. PATENT DOCUMENTS

| | | | |
|---|---|---|---|
| 2012/0130137 A1* | 5/2012 | Orita | B01J 23/002 585/621 |
| 2013/0281748 A1 | 10/2013 | Cha et al. | |
| 2015/0191403 A1 | 7/2015 | Nakahara et al. | |

FOREIGN PATENT DOCUMENTS

| | | | |
|---|---|---|---|
| JP | 2005536498 A | 12/2005 |
| JP | 2011178719 | 9/2011 |
| JP | 2012077074 | 4/2012 |
| JP | 2012240963 | 12/2012 |
| JP | 2013119530 | 6/2013 |
| KR | 1020070095335 A | 9/2007 |
| KR | 1020130046259 A | 5/2013 |
| KR | 1020140044942 A | 4/2014 |
| WO | 2013002459 A1 | 1/2013 |

* cited by examiner

METHOD FOR PRODUCING BUTADIENE THROUGH OXIDATIVE DEHYDROGENATION REACTION

This application is a National Stage Application of International Application No. PCT/KR2015/004928, filed May 15, 2015, and claims the benefit of Korean Patent Application No. 10-2015-0066060, filed May 12, 2015 and Korean Patent Application No. 10-2014-0067685, filed Jun. 3, 2014, the contents of which are incorporated herein by reference in their entirety for all purposes as if fully set forth below.

TECHNICAL FIELD

The present invention relates to a method for producing butadiene through an oxidative dehydrogenation reaction.

BACKGROUND ART

Butadiene is used as an intermediate product in many petrochemical products in the petrochemical market and, as one of the most important basic fractions in the current petrochemical market, the demand for butadiene and value thereof are steadily increasing.

Methods for producing butadiene include an extraction method from C4 fraction through naphtha cracking, direct dehydrogenation of normal-butene (n-butene), oxidative dehydrogenation of n-butene, etc. However, the production method through naphtha cracking, which is responsible for at least 90% of the butadiene that is introduced on the market, not only has a high energy consumption due to a high reaction temperature, but is also not a dedicated process for processing only butadiene, and thus has a limitation in that basic fractions that are other than butadiene are produced as surplus. In addition, the production method through direct dehydrogenation of normal-butene is not only thermodynamically disadvantageous, but, as an endothermic reaction, requires conditions of high temperature and low pressure in order to produce a high yield of butadiene, and thus is not appropriate in a commercial process for producing butadiene.

Meanwhile, the production method through oxidative dehydrogenation of normal-butene, which uses a reaction that produces butadiene by using oxygen as a reactant to remove two hydrogens from normal-butene, is very advantageous thermodynamically because stable water is produced as a reaction product, and unlike the direct dehydrogenation reaction, is an exothermic reaction. Thus a high yield of butadiene may be obtained at a lower temperature than the direct dehydrogenation reaction. Consequently, the method of producing butadiene through the oxidative dehydrogenation of normal-butene may be an effective production process that is capable of meeting the increasing demand for butadiene.

In such the method for producing butadiene through oxidative dehydrogenation of normal-butene, nitrogen, steam, etc., which are other than the reactants (normal-butene and oxygen), are introduced in order to reduce the danger of explosion, and also to prevent coking of catalyst and remove the heat of reaction. Here, along with butadiene, which is the primary product, carbon monoxide, carbon dioxide, etc., which are byproducts, are secondarily produced, and among the byproducts, carbon monoxide, etc. must be separated and discharged in order to prevent a continuous build up in the process. However, there is a limitation in that, during the discharging, active components, such as oxygen, unreacted raw material (normal-butene), and the produced butadiene, are discharged along with the byproducts to outside of the system.

Typically, air is used as an input source for oxygen ($O_2$) and nitrogen ($N_2$) in the oxidative dehydrogenation reaction, and here, there is a limitation in it being difficult to arbitrarily control an amount of the active components, such as nitrogen, oxygen, unreacted raw material, and butadiene, that are discharged. Therefore, a method is needed that is capable of minimizing the active components that are discharged.

DISCLOSURE OF THE INVENTION

Technical Problem

The present invention, which was conceived to overcome the above limitations in the typical technology, has an objective of providing a method for producing butadiene through an oxidative dehydrogenation reaction, the method being capable of minimizing an amount of active components that are discharged by introducing oxygen ($O_2$) and nitrogen ($N_2$), which are included in the raw material stream, independently from each other to thereby easily regulate a ratio of the oxygen to the nitrogen.

Technical Solution

In order to overcome the above limitations, the present invention provides a method for producing butadiene through an oxidative dehydrogenation reaction, the method including steps for introducing a raw material stream that includes C4 fraction, steam, oxygen ($O_2$), and nitrogen ($N_2$) into a reactor that is filled with a catalyst, to thereby carry out an oxidative dehydrogenation reaction (step a); separating a C4 mixture that includes the butadiene that was obtained from the reactor, and a light gas product (step b); and purifying the butadiene-containing C4 mixture (step c).

The method further includes a step d) for dividing the light gas product of the step b) into a first fraction stream and a second fraction stream to reintroduce the first fraction stream into the reactor and discharge the second fraction stream to outside of the system. The first fraction stream includes one or more of nitrogen and carbon dioxide.

Advantageous Effects

A production method according to the present invention may easily regulate an input ratio between oxygen and nitrogen included in a raw material stream, and may also minimize an amount of active components, such as butadiene, included in a second fraction stream that is discharged to outside of the system, to thereby reduce a loss of the active components.

Here, when the butadiene is produced according to the present invention, raw material costs are reduced, productivity is improved, and an amount of purge, which was discharged to outside of the system, that is incinerated is reduced. Consequently, economic competitiveness of the process may be improved.

BRIEF DESCRIPTION OF THE DRAWINGS

The following drawings accompanying the present specification are examples of exemplary embodiments of the present invention, and together with the above description of the invention, provide better understanding of the technical features of the present invention, and thus the present invention should not be construed as limited to that which is set forth in the drawings.

MODE FOR CARRYING OUT THE INVENTION

Hereinafter, the present invention is described in greater detail in order to provide better understanding thereof.

Terms used in the present specification and claims should not be construed as limited to their typical or dictionary definitions. Rather, based on the principle that the concepts of terms may be appropriately defined by the inventor in such a way which best describes the invention, the terms should only be construed as definitions and concepts which are in accordance with the technical scope of the present invention. In particular, the term "light gas product", which is used throughout the specification including the abstract and claims, may indicate gaseous components, including nitrogen, oxygen, water vapor, carbon dioxide, and carbon monoxide, which are among a reaction product that is produced through an oxidative dehydrogenation reaction. In addition, the term "active component" may indicate components, such as nitrogen, oxygen, unreacted raw material, butadiene, etc., that are active in butadiene producing reaction.

The present invention provides a method for producing butadiene through an oxidative dehydrogenation reaction. By regulating a ratio between oxygen ($O_2$) and nitrogen ($N_2$) in a raw material stream, the method may reduce a loss of active components, such as butadiene, discharged after the reaction to out of the system.

Hereinafter, referring to FIG. 1, description is given of a typical method for producing butadiene through an oxidative dehydrogenation reaction.

Figure 1:
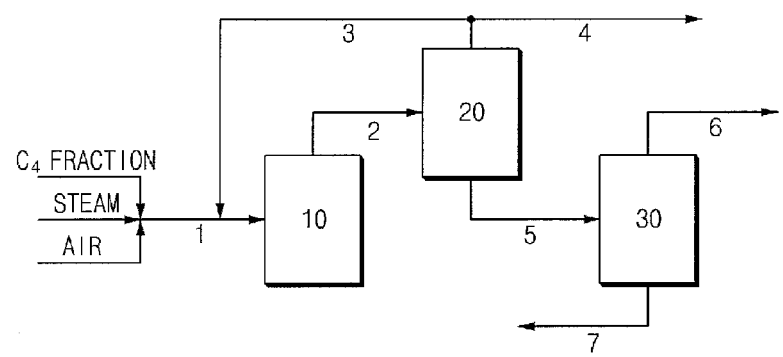
FIG. 1 diagrammatically illustrates a butadiene production process that uses a typically general oxidative dehydrogenation reaction, according to an embodiment of the present invention.

As in FIG. 1, the method for producing butadiene through the oxidative dehydrogenation reaction is typically performed through a production system that includes a raw material input line 1, a reactor 10, a reaction product transport line 2, a gas separator 20, an internal recycle line 3, a discharge line 4, a separated C4 mixture transport line 5, a purification unit 30, and a purified butadiene discharge line 6.

Specifically, the raw material is introduced into the reactor 10 through the raw material input line 1, and the reaction product is obtained through the oxidative dehydrogenation reaction in the reactor 10. The obtained reaction product is introduced into the gas separator 20 through the reaction product transport line 2, and separated into a C4 mixture and light gas product. A portion (for example, nitrogen) of the separated light gas product is recycled through the internal recycle line 3 and reintroduced into the raw material input line 1, and another portion (for example, carbon monoxide) is discharged to outside of the system through the discharge line 4. Moreover, the separated C4 mixture is introduced into the purification unit 30 through the C4 mixture transport line 5 and purified, and thereby the butadiene is produced through the butadiene discharge line 6.

As described above, the oxidative dehydrogenation reaction may be performed when the reactant stream, which includes C4 fraction, steam, oxygen ($O_2$), and nitrogen ($N_2$), is introduced through the raw material input line 1 into the reactor 10 that is filled with a catalyst. The oxidative dehydrogenation reaction is an exothermic reaction, and the main reaction formula may be Formula 1 or 2 which are below.

$$C_4H_8 + \tfrac{1}{2}O_2 \rightarrow C_4H_6 + H_2O \qquad \text{Formula 1}$$

$$C_4H_{10} + O_2 \rightarrow C_4H_6 + 2H_2O \qquad \text{Formula 2}$$

As described above, the method of producing butadiene through the oxidative dehydrogenation reaction includes oxygen as the reaction product, and includes nitrogen, steam, etc. as secondary reaction material in order to reduce a danger of explosion of the reactant, and also to prevent coking of the catalyst and remove the heat of reaction. As a result, along with the butadiene, which is the main reaction product, side reaction products, which include low boiling and water soluble byproducts including carbon monoxide (CO), carbon dioxide ($CO_2$), acetylenes, carbonyls, etc., and high boiling byproducts including phenol and coumarin, are secondarily produced. Among the byproducts, carbon monoxide, etc. must be separated and discharged to prevent a continuous build up from occurring within the process. However, there is a limitation in that the active components, such as the oxygen, unreacted C4 fraction, produced butadiene, etc., are discharged to outside of the system along with the discharged byproducts. In particular, as shown in FIG. 1, in the typical butadiene production method, the oxygen and nitrogen are introduced through air, and the oxygen concentration, in which the explosive range of the reactant was take into account, is regulated by using the introduced air, steam, or by using some of the light gas product that was reintroduced through the internal recycle line 4. The mass ratio of oxygen to nitrogen in air is fixed at 20:78, and since the nitrogen and steam ratios according to the reaction condition in the reactor 10 are also set, it is necessary for the amount of light gas product that is reintroduced to be conditionally determined in order to maintain oxygen concentration. That is, when the concentration of oxygen in the reactor 10 is set by introducing air, the concentration of the nitrogen increases greatly because the mass ratio of nitrogen in air is high, and thus the amount of light gas product, which includes the nitrogen that may be reintroduced into the reactor, is necessarily limited. Therefore, the amount of light gas product that is discarded through the discharge line 4 is greater than the amount of light gas product that is reintroduced. Consequently, there is a limitation of a relatively large amount of the butadiene, unreacted raw material, etc. being discarded, which acts as one of factors that weaken the economic competitiveness of the butadiene production process.

Therefore, in order to overcome limitations of such typical techniques, the production method of the present invention may finely regulate a (mass) flow rate of the oxygen and nitrogen by introducing each of the oxygen and nitrogen in the state of a pure gas, and is characterized by being excessively included in an amount that is greater than that which is required by the reaction.

Specifically, the method for producing butadiene through the oxidative dehydrogenation reaction according to an embodiment of the present invention includes performing the oxidative dehydrogenation reaction by introducing the raw material that includes the C4 fraction, steam, oxygen, and nitrogen into the reactor that is filled with the catalyst (step a); separating the butadiene-containing C4 mixture and the light gas product (step b); and purifying the butadiene-containing C4 mixture (step c).

Moreover, the production method according to an embodiment of the present invention further includes an step d) for fractionating the light gas product that was separated in step b) into a first fraction stream and a second fraction stream to reintroduce the first fraction stream into the reactor and discharge the second fraction stream to outside of the system.

Hereinafter, the production method according to an embodiment of the present invention is described in greater detail with reference to FIG. 2.

Figure 2:
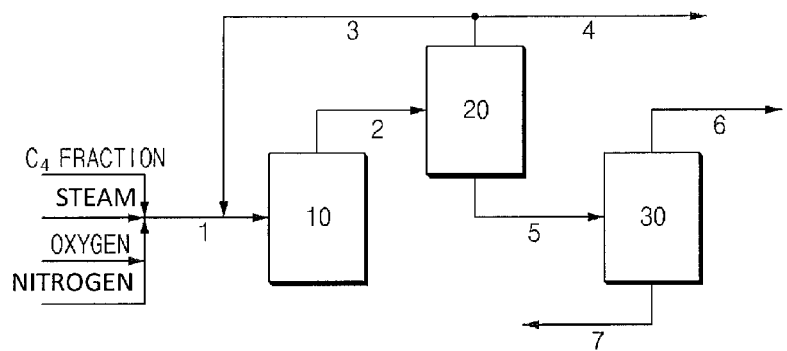
FIG. 2 diagrammatically illustrates a butadiene production process that uses an oxidative dehydrogenation reaction through a method of introducing oxygen and nitrogen as independent pure gasses, according to an embodiment of the present invention.

As shown in FIG. 2, the production method according to the present invention may be performed through a production system that includes the raw material input line 1 for introducing the raw material stream that includes C4 fraction, steam, oxygen, and nitrogen, the reactor 10 that is capable of performing the oxidative dehydrogenation reaction, the reaction product transport line 2 for introducing the reaction product that is obtained from the reactor into the gas separator 20, the gas separator 20 for separating the C4 mixture and light gas product from the reaction product, the internal recycle line 3 for reintroducing the first fraction stream, which includes one or more of nitrogen and carbon dioxide from among the gas product that is separated from the gas separator, into the reactor, the discharge line 4 for discharging the second fraction stream, the C4 mixture transport line 5 for transporting the separated C4 mixture to the purification unit 30, the purification unit 30, and the purified butadiene discharge line 6.

The raw material input line 1 may include individual pipelines for respectively introducing each component of the raw material stream that includes the C4 fraction, steam, oxygen, and nitrogen, or include a plurality of individual pipelines, which are branched out from a single pipeline that is directly connected to the reactor 10, into which the respective components of the raw material stream are individually introduced.

The gas separator 20 is for separating the C4 mixture, which includes the butadiene and the light gas product from the reaction product that is introduced through the reaction product transport line 2, and may include, according to need, one or more of an absorption tower and a dehydration tower.

In addition, the production system for performing the production method according to an embodiment of the present invention may further include a quenching unit that includes a quenching tower, etc. between the reactor 10 and gas separator 20, for cooling the reaction product that is obtained from the reactor; a compressor for compression of the reaction product; a dehydration unit for removing moisture that is included in the reaction product; etc.

In order to obtain the high-purity butadiene, the purification unit 30 may include, according to need, a solvent separation and recovery unit that includes a solvent recovery tower, a high boiler removal column, a solvent purification tower, etc., and a purification tower for purifying the high-purity butadiene.

Hereinafter, the production method according to an embodiment of the present invention is described in further detail by dividing into steps.

The step a is an step for introducing the raw material stream that includes the C4 fraction, steam, oxygen ($O_2$), and nitrogen ($N_2$) into the reactor that is filled with the catalyst to perform the oxidative dehydrogenation reaction.

The reaction may be performed by regulating the reaction conditions inside the reactor to be constant during the entire reaction process, and the reaction condition may be specifically regulated to be a mass ratio of about C4 fraction:steam:oxygen nitrogen=1:0.01 to 10:0.01 to 3:0.01 to 15.

The mass ratio of each active component (C4 fraction, steam, oxygen, and nitrogen) in the reactor may be regulated by the introduced raw material stream and the reintroduced first fraction stream that is described below. Here, the first fraction stream may include one or more of the nitrogen and carbon dioxide as a main component, and may further include the unreacted raw material such as oxygen, steam, etc., other than the main component. That is, the active components (C4 fraction, steam, oxygen, and nitrogen) in the reactor may be a mixture of that which is introduced from the raw material stream, and that which is introduced from the first fraction stream. The mass ratio of the active components may be regulated according to a mass ratio of the active components in the introduced raw material stream and a mass ratio of the active components in the first fraction stream.

In particular, the mass ratio between the oxygen and nitrogen in the reactor is regulated by the mass ratio between the oxygen and nitrogen in the raw material stream and the mass ratio between the oxygen and nitrogen in the reintroduced first fraction stream. Consequently, amount of the first fraction stream that is reintroduced may be dependent on the mass ratio between the oxygen and nitrogen in the introduced raw material stream, and as a result, the discharged amount of the second fraction stream may also be dependent.

A typical production method uses the oxygen and nitrogen included in the raw material stream by introducing the oxygen and nitrogen as air. In this case, the mass ratio between the oxygen and nitrogen in the air is fixed at 0.2:0.78. Thus, the increase in the amount of the air that is introduced in order to regulate the mass ratio of the oxygen, which is the main active component, to the appropriate condition, the greater the increase in mass ratio of nitrogen, which is the secondary active component. As a result, the mass ratio of nitrogen deviates from that of the appropriate condition such that a large amount of nitrogen exists that is not needed in the reaction. Consequently, the amount of the second fraction stream that is discharged to outside of the system increases, and the amount of the first fraction stream that is reintroduced decreases.

Conversely, the production method according to an embodiment of the present invention may introduce the oxygen ($O_2$) and nitrogen ($N_2$), which are included in the raw material stream, independently from each other in the form of a pure gas. The pure gas forms that are independent from each other may indicate that the oxygen ($O_2$) and nitrogen ($N_2$) are respectively introduced as the pure oxygen gas form and pure nitrogen gas form, instead of being introduced from air, which is a mixed gas.

Here, the oxygen may be introduced, as needed, in a form that is mixed with air. That is, in a form in which oxygen is mixed with air (mixed gas form with increased oxygen mass ratio), or by introducing oxygen while mainly introducing air.

Therefore, as described above, through introduction of the oxygen and nitrogen in the form of independent pure gasses instead of in the form of a mixed gas like air, the production method may independently regulate the amount of each component that is included in the raw material stream introduced into the reactor, in particular the amount of one or more component selected from among the oxygen and nitrogen, by measuring in real-time the amounts of active components, etc. included in the reintroduced first stream, the butadiene produced after the reaction, and the second fraction stream that is discharged to outside of the system. Consequently, the total amount of the discharged second fraction stream may be reduced, and thus the amount of the active components, such as butadiene, etc., included in the second fraction stream and discharged to outside of the system may also be regulated and thereby minimized.

The C4 fraction may indicate C4 raffinate-1, 2, or 3 that remains after separation of useful compounds from the C4 mixture that is produced through naphtha cracking, and may also indicate C4s that may be obtained through ethylene dimerization. In an embodiment of the present invention, the C4 fraction may be one selected from the group consisting of n-butane, trans-2-butene, cis-2-butene, and 1-butene, or a mixture of at least two thereof.

In the oxidative dehydrogenation reaction, the steam or nitrogen ($N_2$) may be a diluting gas introduced in order to decrease the danger of explosion while preventing coking, removing the heat of reaction, etc.

Meanwhile, the oxygen ($O_2$) may react as an oxidant with the C4 fraction to bring about the dehydrogenation reaction.

In an embodiment of the present invention, the method of introducing the raw material stream into the reactor may be the method in which the C4 fraction, steam, oxygen ($O_2$), and nitrogen ($N_2$) are mixed before being introduced into the reactor, and then introduced into the reactor in the form of a mixed reactant; or the method in which each of the C4 fraction, steam, oxygen ($O_2$), and nitrogen ($N_2$) are introduced into the reactor through individual pipelines and then uniformly mixed inside the reactor. Specifically, the raw material stream may be such that the C4 fraction, steam, oxygen ($O_2$) and nitrogen ($N_2$) are introduced into the reactor after being mixed by the mixing unit that is located upstream to the reactor, or the C4 fraction, steam, oxygen ($O_2$), and nitrogen ($N_2$) may be introduced into the reactor by respectively passing through the branched plurality of individual pipelines and then being mixed in the single pipeline that is connected to the reactor (see FIG. 2).

In an embodiment of the present invention, the C4 fraction, steam, oxygen, and nitrogen included in the raw material stream may be introduced into the pipeline in a gaseous state, and the gas may be introduced by being preheated to a temperature that is advantageous for the oxidative dehydrogenation reaction.

In an embodiment of the present invention, the catalyst that is charged in the reactor and allows the oxidative dehydrogenation reaction of the C4 fraction to thereby produce the butadiene is not particularly limited, and may be, for example, a ferrite-based catalyst or a bismuth molybdate-based catalyst.

In an embodiment of the present invention, the catalyst may be the bismuth molybdate-based catalyst, the bismuth molybdate-based catalyst may be one or more selected from the group consisting of bismuth, molybdenum, and cobalt, and the bismuth molybdate-based catalyst may also be a multicomponent bismuth molybdate catalyst. However, the type and amount of the reaction catalyst may change according to the specific conditions of the reaction.

In an embodiment of the present invention, the reactor in which the oxidative dehydrogenation reaction may be performed is not particularly limited. The reactor may be, for example, a tubular reactor, a tank reactor, or a fluidized bed reactor. In another example, the reactor may be a fixed bed reactor, and may also be a multitubular fixed bed reactor or a plate-type fixed bed reactor.

The step b) is for separating the main reaction product from the mixed reaction product that includes the butadiene-containing main reaction product and secondarily produced byproduct that are obtained from the reactor, and is the step for separating the butadiene-containing C4 mixture and the light gas product.

The separation may be performed through one or more steps selected from the group consisting of the compression step in which the compressor is used, the dehydration step in which the dehydration unit is used, and the gas separation step in which the gas separator is used.

Moreover, in the production method according to an embodiment of the present invention, a step for quenching the mixed reaction product that is obtained from the reactor may be performed through the quenching tower. The mixed reaction product that is obtained from the reactor may be in the form of a high temperature gas, and accordingly, requires cooling before being introduced into the gas separator.

The cooling method that is used in the quenching step is not particularly limited but, for example, the cooling method in which the coolant directly contacts the mixed reaction product may be used, and the cooling method in which the coolant indirectly contacts the mixed reaction product may also be used.

Specifically, the separation step according to an embodiment of the present invention may contact the mixed reaction product, which is obtained from the reactor, with the absorption solvent in the absorption tower to selectively absorb only the butadiene-containing C4 mixture in the absorption solvent, and to separate and remove the light gas product that is other than the butadiene-containing C4 mixture.

In detail, when the mixed reaction product that is obtained from the reactor makes counter flow contact in the absorption tower with the absorption solvent, the butadiene-containing C4 mixture is selectively absorbed by the absorption solvent, and the remaining light gas product exits through the top of the absorption tower, via the piping.

The type of the absorption tower is not particularly limited and may be, for example, a packed tower, a wetted wall tower, a spray tower, a cyclone scrubber, a bubble tower, a bubble agitation tank, a tray tower (bubble cap tower, perforated plate tower), or a foam separation tower.

The absorption solvent that is typically used in the technical field may be used and, for example, saturated hydrocarbons C6 to C10, aromatic hydrocarbons C6 to C8, amide compounds, etc. may be used. The absorption solvent may be, for example, dimethylformamide (DMF), toluene, xylene, n-methyl-2-pyrrolidone (NMP), etc.

Meanwhile, in an embodiment of the present invention, the light gas product that is discharged through the top of the absorption tower via the piping may be divided into the first fraction stream and the second fraction stream. The first fraction stream may be, as described above, a concentrated stream that includes one or more selected from the group consisting of nitrogen and carbon dioxide, and may be recycled along the internal recycle line 3 (see FIG. 2) to be reintroduced into the reactor (step d). In addition to the above described components, oxygen, steam, unreacted raw material, butadiene, etc. may be further included in the first fraction stream. The carbon dioxide that is included in the first fraction stream may be reintroduced through internal recycling into the reactor, and function as a mild oxidant in the oxidative dehydration reaction, or as the diluting gas.

Meanwhile, the second fraction stream is a purge stream that is discharged to outside of the system and is discharged to outside of the system through the discharge line 4 that is separate from the first fraction stream (see FIG. 2, step d). The second fraction stream may include nitrogen ($N_2$), carbon dioxide (CO$_2$), unreacted raw material, butadiene, etc. The mass of the butadiene that is included in the second fraction stream and thereby discharged to outside of the system may be an amount that is equivalent to about 0.01% to about 10% of the total amount of the butadiene that is produced through the oxidative dehydrogenation reaction in the reactor.

In an embodiment of the present invention, the absorption solvent is used for selectively absorbing only the butadiene-containing C4 mixture, but may also dissolve some gasses such as nitrogen, carbon dioxide, etc. Here, the gas stripping step for removing gasses such as the nitrogen, carbon dioxide, etc. may be further performed, and the gas stripping step may be performed in a gas stripper.

In the gas stripping step, the gas stripping method is not particularly limited, and may be a typical method that is used in the field.

The step c is a step for purifying the butadiene-containing C4 mixture in order to obtain the high-purity butadiene. The purifying step may be performed through one or more equipment selected from among the solvent recovery tower for separating and recovering the absorption solvent, a high boiler removal column for removing high boiling part components, solvent separation and recovery equipment including the solvent purification tower, and the butadiene purification tower for purifying the high-purity butadiene.

In an embodiment of the present invention, a method for separation and recovery of the solvent is not particularly limited and, for example, a distillative separation method may be used. According to the distillative separation method, after the absorption solvent in which the butadiene-containing C4 mixture is dissolved is introduced to the solvent recovery tower, distillative separation is performed by a reboiler and a condenser. After undergoing the distillative separation process, the butadiene-containing C4 mixture is extracted from near the top of the tower.

The absorption solvent that is separated in the above process is extracted from the bottom of the solvent recovery tower, and the extracted absorption solvent may be reused by being reintroduced to the upstream process. Since the absorption solvent may include impurities, a portion may be extracted before recycling, and undergo a process of removing the impurities through a known purification method such as distillation, decantation, sedimentation, contact treatment with an absorption solvent or an ion exchange resin, etc.

In an embodiment of the present invention, the butadiene-containing C4 mixture that is separated from the absorption solvent may be introduced into the high boiler removal column in order to separate the high boiling components.

A process for removing the high boiling components (components with a higher solubility than butadiene) is performed in the high boiler removal column. In the process, the components that have a higher solubility than the butadiene are dissolved in the solvent. The solvent is discharged from the bottom of the column, and may be transported to the solvent purification tower.

Meanwhile, the butadiene from which the high boiling components were removed may be discharged from the top of the high boiler removal column and transported to the butadiene purification tower. In an embodiment of the present invention, the high boiling and low boiling components are removed while the butadiene that was transported to the purification tower goes through the purification tower, and thereby the high-purity butadiene may be obtained. In an embodiment of the present invention, the purity of the butadiene that can ultimately be obtained through the above series of steps may be about 99.0% to about 99.9%.

EXAMPLES

Hereinafter, the present invention will be described in more detail through examples. The examples are merely for illustrating embodiments of the present invention, and it will be obvious to those with ordinary skill in the art that the scope of the present invention is not limited by the examples.

Example 1

An oxidative dehydrogenation reaction was performed by introducing a raw material stream into a reactor that is filled with a bismuth molybdate-based catalyst.

A metal tubular reactor was used as the reactor. 1-butene, steam, oxygen, and nitrogen were used as the raw materials. The initial raw material input ratio was introduced by being regulated such as to be appropriate for the reaction condition. Afterwards, the mass ratios between oxygen and nitrogen were introduced as shown in Table 1. The reaction condition was regulated to be a mass ratio of 1-butene:stream:oxygen:nitrogen=1:3:0.5:9. The reaction system was designed such that steam was introduced into the reactor by being mixed with the other raw materials. An amount of the 1-butene was controlled by using a liquid mass flow controller, amounts of oxygen and nitrogen were controlled by using a gas mass flow controller, and an amount of steam was controlled by using a liquid pump to regulate an input rate. After the reaction, a mixed reaction product was separated into a butadiene-containing C4 mixture and a light gas product through a separation unit. The butadiene-containing C4 mixture was then purified through a purification unit, and thereby the butadiene of 99.7% purity was produced (yield 99.4%).

In addition, a portion of the separated light gas product was discharged to outside of the system through a purge stream (a second fraction stream). Among active components that were included in the purge stream and thus discharged to outside of the system, the amount of the butadiene was equivalent to about 0.06% of the amount of the butadiene that was produced through the oxidative dehydrogenation reaction in the reactor.

Example 2

Other than, after the initial introduction, mass ratios of the introduced oxygen and nitrogen being regulated as shown in the below Table 1, the butadiene of 99.7% purity was produced through the same method as the above Example 1 (yield 99.3%). Meanwhile, among the active components that were discharged to outside of the system, the amount of the butadiene was equivalent to about 0.2% of the amount of the butadiene that was produced through the oxidative dehydrogenation reaction in the reactor.

Comparative Example 1

Other than introducing the oxygen and nitrogen as air, which is a mixed gas, the butadiene of 99.7% purity was produced through the same method as the above Example 1 (yield 99.0%). Here, the mass ratio of oxygen to nitrogen in air was 0.3:1. Moreover, among the active components that were discharged to outside of the system, the amount of the butadiene was equivalent to about 0.5% of the amount of the butadiene that was produced through the oxidative dehydrogenation reaction in the reactor.

Here, the final recovery rate of the butadiene was 99.0%

TABLE 1

| Classification | | Example 1 | Example 2 | Comparative Example 1 |
|---|---|---|---|---|
| Mass ratio of externally introduced oxygen ($O_2$) to nitrogen ($N_2$) | | 3.28 | 0.78 | 0.30 |
| Mass ratio inside reactor | Ratio of steam to C4 fraction | 0.98 | 0.98 | 0.98 |
| | Ratio of oxygen ($O_2$) to C4 fraction | 0.49 | 0.49 | 0.49 |
| | Ratio of nitrogen ($N_2$) to C4 fraction | 3.93 | 5.07 | 5.36 |
| Ratio of discharged butadiene to net butadiene created | | 0.0006 | 0.002 | 0.005 |
| Final butadiene recovery rate | | 99.4 | 99.3 | 99.0 |

TABLE 2

Second fraction stream 4

| Classification | | Example 1 | Example 2 | Comparative Example 1 |
|---|---|---|---|---|
| Total flow (ton/hr) | | 5.79 | 17.13 | 41.52 |
| Mass ratio (wt %) | C4 fraction | 1.82 | 0.8 | 0.5 |
| | Oxygen | 1.62 | 1.8 | 1.9 |
| | Nitrogen | 57.96 | 84.2 | 92 |
| | Carbon dioxide | 37.31 | 12.4 | 4.9 |
| | Butadiene | 0.26 | 0.3 | 0.3 |
| | Other | 1.03 | 0.52 | 0.3 |

The results of the above Tables 1 and 2 were measured during a continuous process at a particular identical point in time after the initial reaction process. The first reaction was performed by introducing the raw material streams that had identical mass ratios, and all of the total flow rates that were being introduced into the reactor were identical. Ratios of the respective components were obtained through gas chromatography-mass spectrometry.

As in the results of the above Tables 1 and 2, in Examples 1 and 2, which are in accordance to an embodiment of the present invention, the oxygen and nitrogen may be introduced independently into the reactor, such that the mass ratios between the oxygen and nitrogen may be flexibly regulated. Thus, it is confirmed that the mass ratio of the nitrogen inside the reactor may be more easily regulated than in Comparative Example 1, in which the oxygen and nitrogen are introduced as air. Moreover, it was confirmed that the total flow rate (Table 2) of the second fraction stream may be regulated by flexibly regulating the mass ratios between the oxygen and nitrogen that are introduced. Consequently, it was confirmed that, through regulation of the total amount of the second fraction stream that is discharged to outside of the system, the amount of the butadiene that is included therein to be discharged to outside of the system may be regulated.

The invention claimed is:

1. A method for producing butadiene through an oxidative dehydrogenation reaction, the method comprising:
   a) a step for introducing a raw material stream that includes a C4 fraction, steam, oxygen ($O_2$), and nitrogen ($N_2$) into a reactor that is filled with a catalyst to perform the oxidative dehydrogenation reaction to yield a mixed reaction product that includes:
      a C4 mixture containing the butadiene; and
      a light gas product comprising carbon dioxide produced through the oxidative dehydrogenation reaction, oxygen and nitrogen;
   b) a step for separating the mixed reaction product into a separated C4 mixture that includes the butadiene and the light gas product;
   c) a step for purifying the separated C4 mixture to produce and recover purified butadiene;
   d) step for separating the light gas product into:
      a first fraction stream comprising one or more of the nitrogen, the oxygen and the carbon dioxide; and
      a second fraction stream;
   reintroducing the first fraction stream into the reactor; and
   discharging the second fraction stream to outside of the system,
   wherein:
      the oxygen ($O_2$) and nitrogen ($N_2$) included in the raw material stream are independently introduced in pure gas state;
      a total amount of the first fraction stream reintroduced into the reactor is regulated according to mass ratios between the oxygen and nitrogen in the raw material stream; and
      the mass ratios between the oxygen and nitrogen in the raw material stream are regulated independently of each other.

2. The method of claim 1, wherein the oxygen ($O_2$) included in the raw material stream is introduced in a mixed state with air.

3. The method of claim 1, wherein a reaction condition in the reactor is a mass ratio of about C4 fraction:steam:oxygen:nitrogen=1:1 to 9:0.01 to 3:3 to 9.

4. The method of claim 1, wherein the carbon dioxide ($CO_2$) is reintroduced into the reactor as a mild oxidant or a diluting gas.

5. The method of claim 1, wherein:
   a total amount of the butadiene that is lost is regulated in proportion to a total amount of the second fraction stream.

6. The method of claim 5, wherein the total mass of the butadiene that is lost is 0.01% to 10% of a total mass of the butadiene that is produced by the oxidative dehydrogenation reaction.

7. The method of claim 1, wherein the C4 fraction is at least one selected from among the group consisting of n-butane, trans-2-butene, cis-2-butene, and 1-butene.

* * * * *